United States Patent
Miguens Pereira et al.

(10) Patent No.: US 8,592,404 B2
(45) Date of Patent: Nov. 26, 2013

(54) DERIVATIVES OF PORPHYRIN, PARTICULARLY CHLORINS AND/OR BACTERIOCHLORINS, AND USES THEREOF IN PHOTODYNAMIC THERAPY

(75) Inventors: Maria Miguens Pereira, Coimbra (PT); Luis Guilherme Arnaut Moreira, Coimbra (PT); Sebastiao Jose Formosinho Simoes, Coimbra (PT); Carlos Monteiro, Coimbra (PT)

(73) Assignee: Universidade de Coimbra, Coimbra (PT)

( * ) Notice: Subject to any disclaimer, the term of this patent is extended or adjusted under 35 U.S.C. 154(b) by 1502 days.

(21) Appl. No.: 11/719,295

(22) PCT Filed: Nov. 10, 2005

(86) PCT No.: PCT/EP2005/012212
§ 371 (c)(1),
(2), (4) Date: Jun. 20, 2007

(87) PCT Pub. No.: WO2006/053707
PCT Pub. Date: May 26, 2006

(65) Prior Publication Data
US 2009/0149525 A1    Jun. 11, 2009

(30) Foreign Application Priority Data
Nov. 16, 2004   (FR) ..................................... 04 12149

(51) Int. Cl.
*A01N 55/02* (2006.01)
*A01N 43/36* (2006.01)
*A61K 31/40* (2006.01)
*C07B 47/00* (2006.01)
*C07D 487/22* (2006.01)

(52) U.S. Cl.
USPC ............................ 514/185; 514/410; 540/145

(58) Field of Classification Search
USPC .................................. 540/145; 514/185, 410
See application file for complete search history.

(56) References Cited

U.S. PATENT DOCUMENTS

| 5,876,989 A | 3/1999 | Berg et al. |
| 6,114,321 A | 9/2000 | Platzek et al. |

FOREIGN PATENT DOCUMENTS

| WO | WO 98/50386 | 11/1998 |
| WO | WO 03/008430 | 1/2003 |
| WO | WO 03/020309 | 3/2003 |

OTHER PUBLICATIONS

Banfi et al., "Oxidative Cleavage . . . ", BioOrg & Med. Chem., 11 (2003) 3595-3605.*
Molinari et al., "Phororedox and photocatalytic . . . ", J'nal of Mol. Cat. A: Chemical 158 (2000) 521-531.*
Luksiene, Zivile, "Photodynamic therapy: mechanism of action and ways to improve the efficiency of treatment", Medicina, 2003, vol. 39 tomas, No. 12, pp. 1137-1150.
Sternberg et al., "Porphyrin-based Photosensitizers for Use in Photodynamic Therapy", Tetrahedron, 1998, vol. 54, pp. 4151-4202.

* cited by examiner

Primary Examiner — Paul V. Ward
(74) Attorney, Agent, or Firm — Young & Thompson

(57) ABSTRACT

The invention relates to derivatives of porphyrin, particularly chlorins and/or bacteriochlorins, which can be used in photodynamic therapy. According to the formulas of the invention, $X^1$, $X^2$, $X^3$, $X^4$, $X^5$, $X^6$, $X^7$, $X^8$, which may be identical or different, each represent halogen atoms or hydrogen atoms. $R^1$, $R^2$, $R^3$, $R^4$, which may be identical or different, are each selected from the following groups: —OH, amino acids, —OR and —NHR and/or a chlorine atom, wherein R is an alkyl group having between 1 and 12 carbon atoms. The invention also relates to an anticancer and/or antiviral and/or antimicrobial medicament for human or animal use, which contains one or more compounds as the main active ingredient.

28 Claims, 2 Drawing Sheets

DERIVATIVES OF PORPHYRIN, PARTICULARLY CHLORINS AND/OR BACTERIOCHLORINS, AND USES THEREOF IN PHOTODYNAMIC THERAPY

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

Photodynamic therapy (PDT) is a technique used for treating several types of diseases, in particular, certain types of cancer. Such a technique consists of marking the pathological tissues with a photosensitizer, then causing selective destruction of said tissues while exposing them to a light source of a specific wavelength. Such monochromatic light is generally produced by a laser or a laser diode.

2. Description of Related Art Including Information Disclosed Under 37 CFR 1.97 and 37 CFR 1.98

A photosensitizer is understood to mean any molecule liable to store light energy, being activated by said energy and lending itself therefore to numerous biochemical combinations.

The photosensitizer, generally between 0.1 and 0.5 micromole/kg of body mass, is delivered to the patient, then picked up by the cells of the whole organism. The photosensitizing molecule accumulates preferably in cancerous cells, but remains inactive until exposed to a light of appropriate wavelength. The illumination or irradiation of the tumour by light activates the molecule, which then interacts with oxygen and forms a transient substance, in particular singlet oxygen. Singlet oxygen is a very reactive and toxic molecule which destroys the cancerous cells wherein the photosensitizer has concentrated.

A certain time elapses between the delivery of the photosensitizer and its activation by means of the laser light. The laser light used in photodynamic therapy is focused by means of an optic fiber and is applied only for a few minutes. The practitioner holds the optic fiber in close vicinity of the cancer so as to deliver the correct amount of light. Consequently, photodynamic therapy only damages the healthy cells minimally.

At the initial stage of a cancer, the objective of such a technique may consist of completely eliminating and curing the cancer but, at an advanced stage, it may consist of reducing the volume of the tumour in order to alleviate symptoms. New normal cells replace those destroyed by photodynamic therapy, which enables rapid healing after treatment and avoids particularly ungracious scars which may form with other ablation of tissues.

Even patients already treated by surgery, radiotherapy or chemotherapy may be subjected to this technique reliably.

By way of examples of diseases which may be treated by photodynamic therapy, one may quote in particular stomach, intestine, lung, breast, uterus, esophagus, ovary, pancreas, liver, bladder, bile, tongue, brain, skin, thyroid, prostate, parotid gland cancer, as well as certain viral and/or microbial diseases.

Photodynamic therapy may also be used as a means for diagnosing certain forms of cancer. In this view, it suffices that the photosensitizing molecules are fluorescent and, hence, capable of emitting light when they receive a radiation.

At the moment, the use of certain porphyrin derivatives, in particular hematoporphyrin, as photosensitizers is known in photodynamic therapy. This agent, known under the trademark Photofrin™, registered by AXCAN PHARMA INC., is a purified mixture of hematoporphyrin. Hematoporphyrin is in turn a derivative of porcine hemoglobin.

Besides, Photofrin™ has been the sole photosensitizing molecule until now, which has been authorized for marketing in several countries and, in particular, in France, for treating esophageal cancer.

In spite of the advantages shown by Photofrin™, such as its solubility in an aqueous medium, a good output of singlet oxygen formation and an easy synthesis, it still exhibits a few shortcomings.

First of all, Photofrin™ is activated by a 630 nm light. Still, at such a wavelength, the penetration of light into the tissues only ranges from 5 to 10 mm, which exhibits a severe handicap when tumours are wider and deeper. Moreover, such a photosensitizer causes cutaneous photosensitivity up to six weeks after treatment. Finally, the fact, that Photofrin™ is a mixture of several molecules, makes the choice of the appropriate dosimetry more difficult, as well as the choice of the photosensitizer of the light delivered.

Among other compounds under study, so-called second generation compounds, the document WO-98/50386 describes certain benzoporphyrine derivatives. Such derivatives exhibit certain advantages relative to Photofrin™ in that they absorb light at a 690 nm wavelength and, consequently, may be used in the treatment of wider and deeper cancers. Such derivates exhibit moreover better selectivity against cancerous cells.

However, certain problems associated with selectivity, light absorption and toxicity persist.

BRIEF SUMMARY OF THE INVENTION

The purpose of the present invention is to offer new porphyrin derivatives, such as in particular chlorins and/or bacteriochlorins which remedy the shortcomings aforementioned, in particular with regard to preferential accumulation in cancerous cells, better stability and lower phototoxicity.

Another aim of the present invention is to offer an anti-cancerous and/or anti-viral and/or anti-microbial medication in order to be used in photodynamic therapy.

Other aims and advantages of the invention will appear in the following description which is given only by way of example and without being limited thereto.

The present invention relates to a porphyrin derivative, in particular chlorin, of formula:

FORMULA (I)

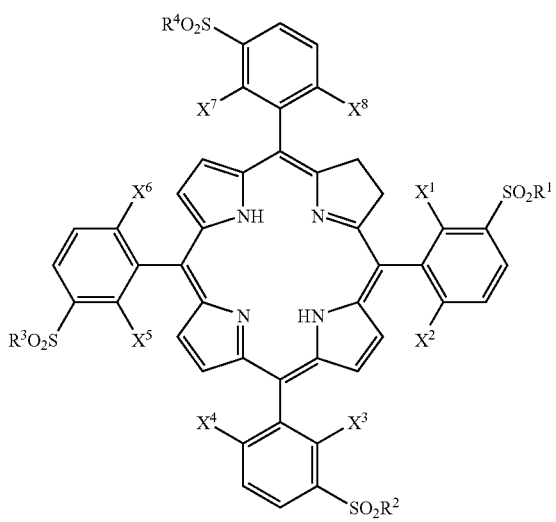

wherein:
$X^1$ $X^2$, $X^3$, $X^4$, $X^5$, $X^6$, $X^7$, $X^8$ are each, identical or different, selected among halogen atoms and/or hydrogen atoms; and
$R^1$, $R^2$, $R^3$, $R^4$ are each, identical or different, selected among the moieties: —OH, amino acids, —OR and —NHR and/or chlorine atom, wherein R is an alkyl moiety having 1 to 12 carbon atoms.

The present invention also relates to a porphyrin derivative, in particular bacteriochlorin, of formula:

FORMULA (II)

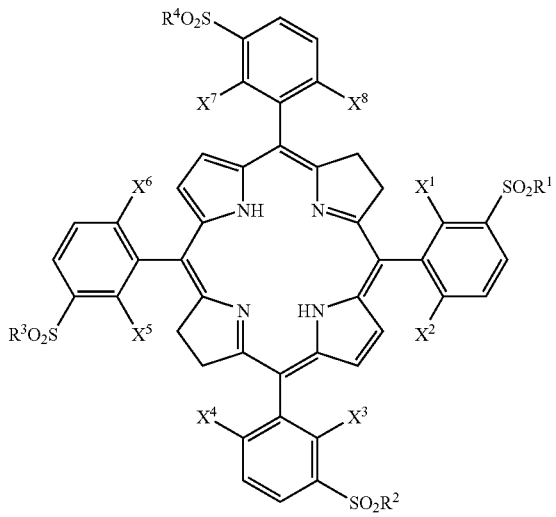

wherein:
$X^1$ $X^2$, $X^3$, $X^4$, $X^5$, $X^6$, $X^7$, $X^8$ are each, identical or different, selected among halogen atoms and/or hydrogen atoms; and
$R^1$, $R^2$, $R^3$, $R^4$ are each, identical or different, selected among the moieties; —OH, amino acids, —OR and —NHR and/or chlorine atom, wherein R is an alkyl moiety having 1 to 12 carbon atoms.

One of the advantages of these derivatives lies in the presence of the chlorosulfonyl moiety in the molecule, as described in the present invention, which enables simple and efficient introduction to a large variety of chemical moieties.

The present invention relates, moreover, to an anticancerous and/or antiviral and/or antimicrobial medication for human or animal usage exhibiting as a main active agent one or several compounds described in the present invention.

BRIEF DESCRIPTION OF THE SEVERAL VIEWS OF THE DRAWINGS

The invention will be understood better when reading the following description, accompanied by the appended drawings.

DETAILED DESCRIPTION OF THE INVENTION

The present invention relates first of all to a porphyrin derivative, in particular chlorin, of formula:

FORMULA (I)

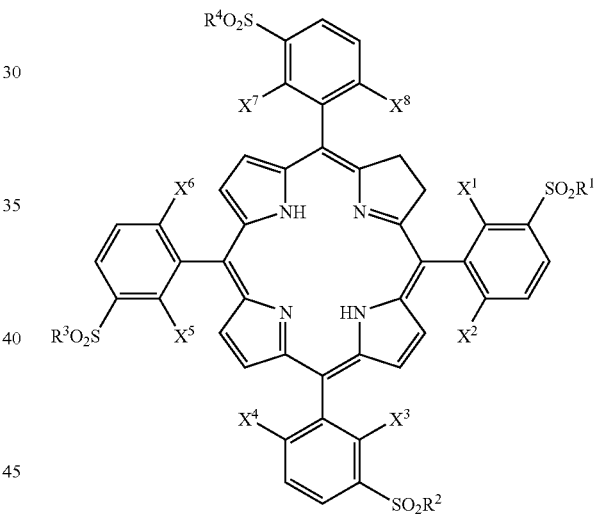

wherein:
$X^1$ $X^2$, $X^3$, $X^4$, $X^5$, $X^6$, $X^7$, $X^8$ are each, identical or different, selected among halogen atoms and/or hydrogen atoms; and
$R^1$, $R^2$, $R^3$, $R^4$ are each, identical or different, selected among the moieties; —OH, amino acids, —OR and —NHR and/or chlorine atoms, wherein R is an alkyl moiety having 1 to 12 carbon atoms.

One of the advantages of such type of derivatives lies in that they are amphiphile. The amphiphilic character is essential so that the molecules may cross the cellular membrane and accumulate inside the cells.

"Amphiphilic" is understood to mean any molecule which exhibits both a hydrophilic and hydrophobic character.

Figure 1:
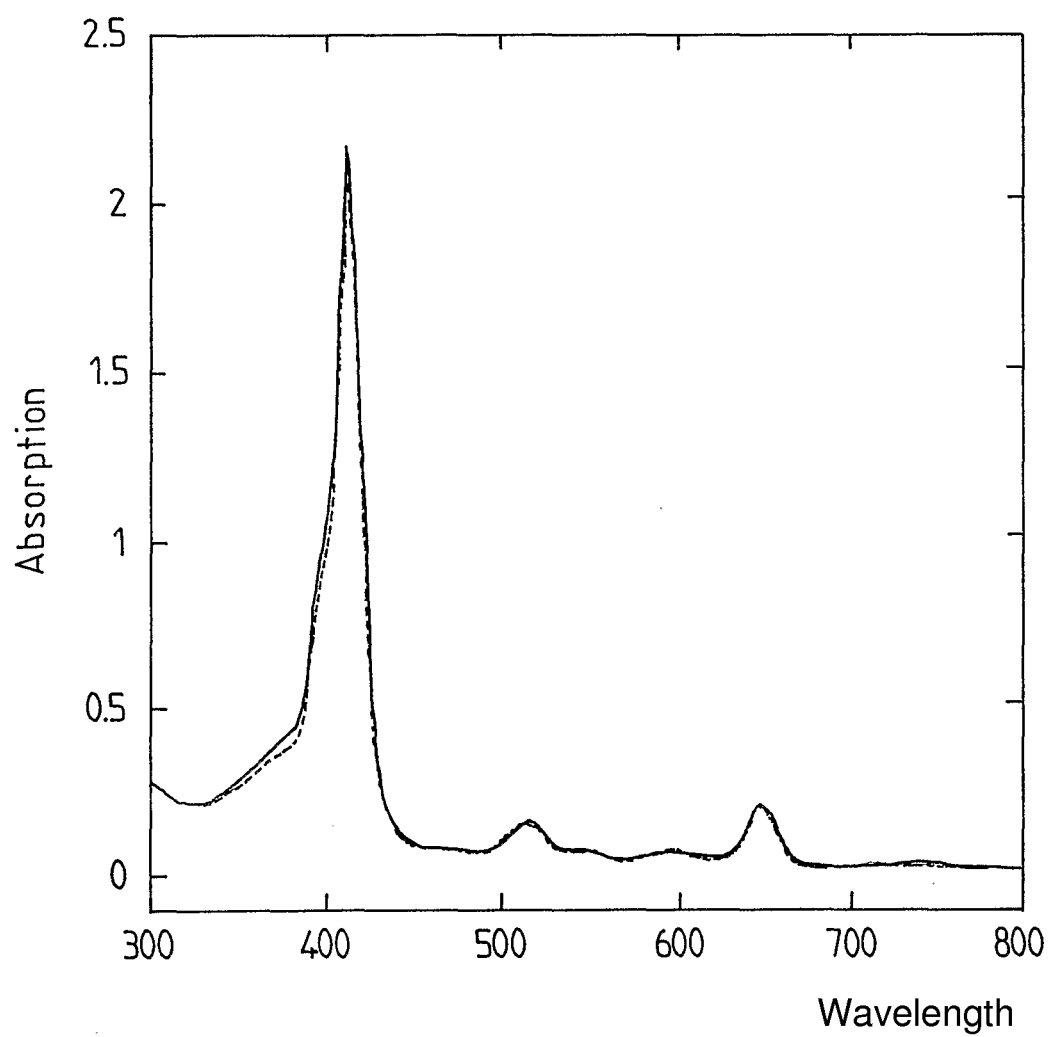
FIG. 1 represents the absorption spectrum of chlorin according to the Formula (I) in an aqueous solution before (full line) and after (dotted line) irradiation of the sample by the second harmonic of a laser Nd: YAG.

These types of derivatives exhibit an absorption band at 650 nm, as shown on FIG. 1.

The present invention also relates to the derivatives complying with Formula (I), wherein:
$X^1$ $X^2$, $X^3$, $X^4$, $X^5$, $X^6$, $X^7$, $X^8$ are each, identical or different, selected among halogen atoms, and/or hydrogen atoms, such that at least one of the radicals X of each pair $X^1/X^2$, $X^3/X^4$, $X^5/X^6$, $X^7/X^8$ is a halogen atom.

An advantage of this particular type of derivative lies in the presence of the halogen atoms in the ortho positions of the phenyl moiety which increases the quantum yield of the formation of the triplet state, without reducing significantly the lifetime thereof. With higher quantum yield, the triplet state may transfer its energy more efficiently towards oxygen with consequently higher yield in the formation of singlet oxygen.

Moreover, the halogen atoms in the ortho positions of the phenyl moiety make the tetrapyrolic macrocycle more stable and, hence, more efficient in its use in photodynamic therapy.

Still according to the present invention, and in compliance with Formula (I):
$X^2$, $X^4$, $X^6$ and $X^8$ are either chlorine atoms, or fluorine atoms;
$X^1$, $X^3$, $X^5$ and $X^7$ are hydrogen atoms; and
$R^1$, $R^2$, $R^3$, $R^4$ are chlorine atoms.

According to another variation of the present invention, and in compliance with Formula (I):
$X^2$, $X^4$, $X^6$ and $X^8$ are either chlorine atoms, or fluorine atoms;
$X^1$, $X^3$, $X^5$ and $X^7$ are hydrogen atoms; and
$R^1$, $R^2$, $R^3$, $R^4$ are —OH moieties.

The present invention also relates to derivatives complying with Formula (I), wherein:
$X^1$ $X^2$, $X^3$, $X^4$, $X^5$, $X^6$, $X^7$, $X^8$ are chlorine atoms; and
$R^1$, $R^2$, $R^3$, $R^4$ are either chlorine atoms, or —OH moieties.

The present invention also relates to a porphyrin derivative, in particular bacteriochlorin, of formula:

FORMULA (II)

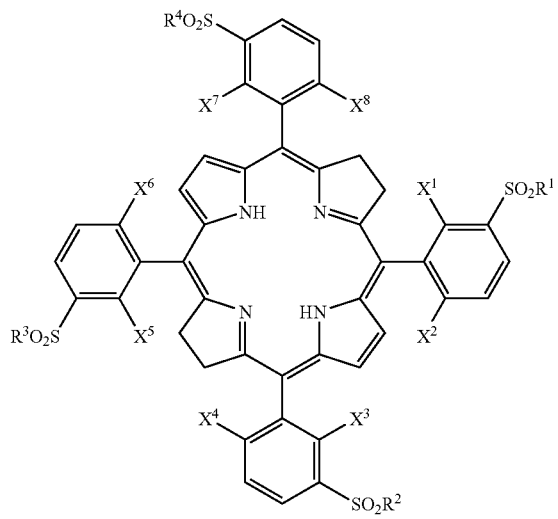

wherein:
$X^1$ $X^2$, $X^3$, $X^4$, $X^5$, $X^6$, $X^7$, $X^8$ are each, identical or different, selected among halogen atoms, and/or hydrogen atoms; and
$R^1$, $R^2$, $R^3$, $R^4$ are each, identical or different, selected among the moieties: —OH, amino acids, —OR and —NHR and/or chlorine atom, wherein R is an alkyl moiety having 1 to 12 carbon atoms.

An advantage of such types of derivatives, and for the case of chlorins described above, lies in that they are also amphiphilic.

Figure 2:
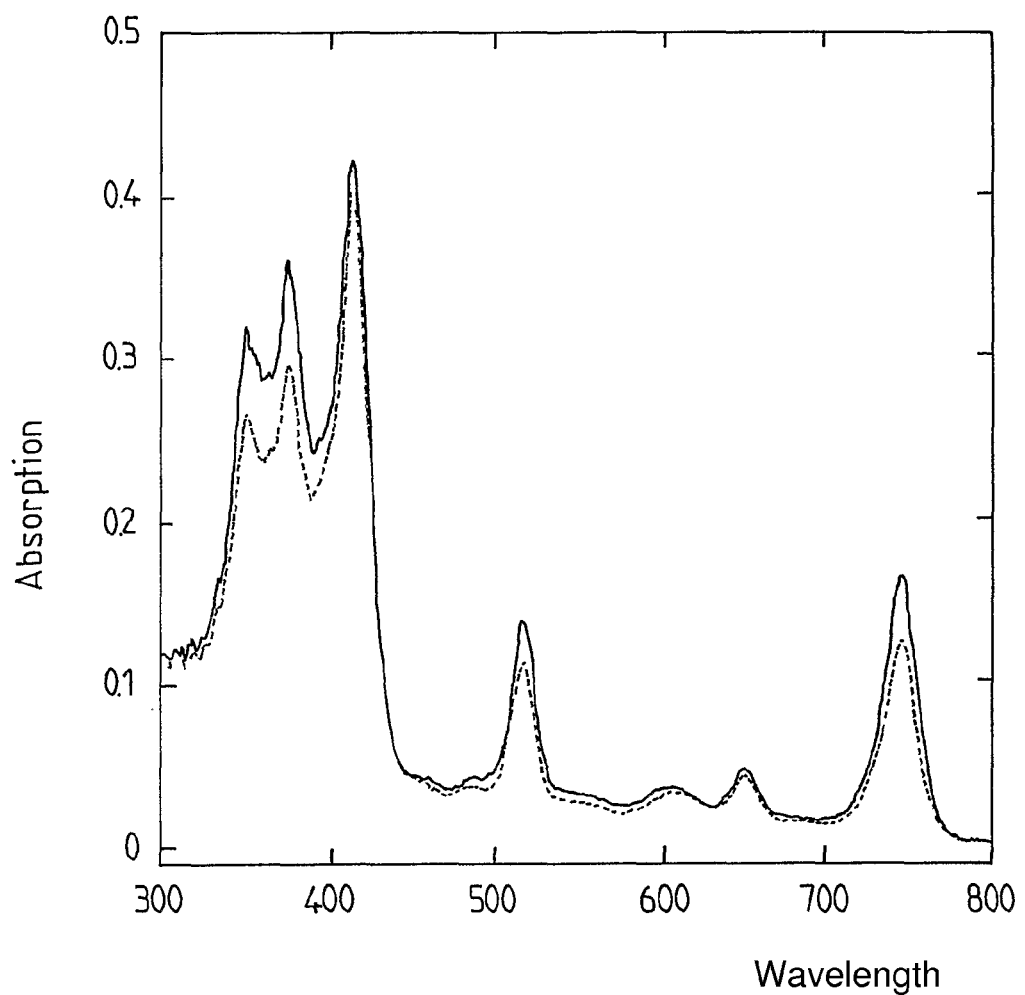
FIG. 2 represents the absorption spectrum of bacteriochlorin according to the Formula (II) in an aqueous solution before (full line) and after (dotted line) irradiation of the sample by the second harmonic of a laser Nd: YAG.

Another advantage of these derivatives, in particular, bacteriochlorin complying with the Formula (II), consists of absorbing light in the red region at 750 nm, as illustrated on FIG. 2. At such a wavelength, the shielding effects caused by human tissues, in particular by hemoglobin, are not so high, which enables increase of the 'amount' of light reaching the photosensitizers inside the cells.

The present invention also relates to the derivatives complying with Formula (II), wherein:
$X^1$ $X^2$, $X^3$, $X^4$, $X^5$, $X^6$, $X^7$, $X^8$ are each, identical or different, selected among halogen atoms, and/or hydrogen atoms, such that at least one of the radicals X of each pair $X^1/X^2$, $X^3/X^4$, $X^5/X^6$, $X^7/X^8$ is a halogen atom.

As for the case of chlorin described above, the presence of the halogen atoms in the ortho positions of the phenyl moiety, increases the quantum yield of the formation of the triplet state, without reducing significantly the lifetime thereof, and consequently, also increases the increase in the formation of the singlet oxygen.

The present invention also relates to certain derivatives, complying with Formula (II), wherein:
$X^2$, $X^4$, $X^6$ and $X^8$ are either chlorine atoms, or fluorine atoms;
$X^1$, $X^3$, $X^5$ and $X^7$ are hydrogen atoms; and
$R^1$, $R^2$, $R^3$, $R^4$ are chlorine atoms.

According to another variation of the present invention, and in compliance with Formula (II):
$X^2$, $X^4$, $X^6$ and $X^8$ are either chlorine atoms, or fluorine atoms;
$X^1$, $X^3$, $X^3$ and $X^7$ are hydrogen atoms; and
$R^1$, $R^2$, $R^3$, $R^4$ are —OH moieties.

The present invention relates moreover to derivatives complying with Formula (II), wherein:
$X^1$ $X^2$, $X^3$, $X^4$, $X^5$, $X^6$, $X^7$, $X^8$ are chlorine atoms; and
$R^1$, $R^2$, $R^3$, $R^4$ are either chlorine atoms, or —OH moieties.

The presence of the halogen atoms in the ortho positions of the phenyl moiety also makes the tetrapyrrolic macrocycle and its derivatives more stable.

According to the present invention, the halogen atoms are fluorine and/or chlorine and/or bromine.

Another aim of the present invention consists in the method of preparation of derivatives as described above including the following steps:
a chlorosulfonation step of the corresponding halogenated porphyrin;
a reducing step of the halogenated and chlorosulfonated porphyrin to chlorin and/or to bacteriochlorin with hydrazide and in the presence of organic hindered bases; and
a coupling step between the chlorosulfonated moiety and amines and/or amino acids and/or alcohols, or hydrolysing the chlorine of the chlorosulfonated moiety with water.

By way of non-limiting example, the chemical synthesis of the derivative complying with Formula (I) wherein:
$X^2$, $X^4$, $X^6$ and $X^8$ are chlorine atoms;
$X^1$, $X^3$, $X^5$ and $X^7$ are hydrogen atoms,
$R^1$, $R^2$, R, $R^4$ are —OH moieties.
was conducted as follows:
5,10,15,20-tetrakis (2-chloro-3-chlorosulfonylphenyl) porphyrin (0.0658 g, 6.55×10$^{-5}$ mol) was dissolved in N.N-dimethylformamide and/or toluene, and/or pyridine and/or picoline (50 mL) dried and distilled beforehand, and the temperature of the reactive mixture was raised from 50° C. to 150° C. Then, a solution of p-toluene sulfonyl hydrazide (5.5×10$^{-5}$ mol) and a bulky organic base, such as DABCO and/or DBU in DMF (5 mL) was added to the reactive mixture. The mixture was stirred at 150° C. under nitrogen atmosphere and in the absence of light.

The evolution of the reaction was followed by spectroscopy of the visible region until the band Q at 650 nm reached its maximum.

Then, the solvent was evaporated and the reactive mixture was treated and the product obtained was hydrolysed with water and purified by solvent-solvent extraction. After re-crystallization with a methanol/ldichlomethane mixture, the product was obtained with an 80% yield.

Mass spectroscopy (FAB), m/z: 1075 (central peak).

Vis-UV (buffer solution NaOH, $KH_2PO_4$), maximal wavelength (in nm): 414, 516, 542, 598, 649.

Fluorescence quantum yield: 0.04

Lifetime of the triplet state in a nitrogen-saturated aqueous solution: 235 µs

Lifetime of the triplet state in an air-saturated aqueous solution: 3.88 µs quantum yield of the formation of singlet oxygen in a deuterated aqueous solution: 0.56.

Lifetime of singlet oxygen: 65 µs in deuterated water

Schematically the reaction may be described as follows:

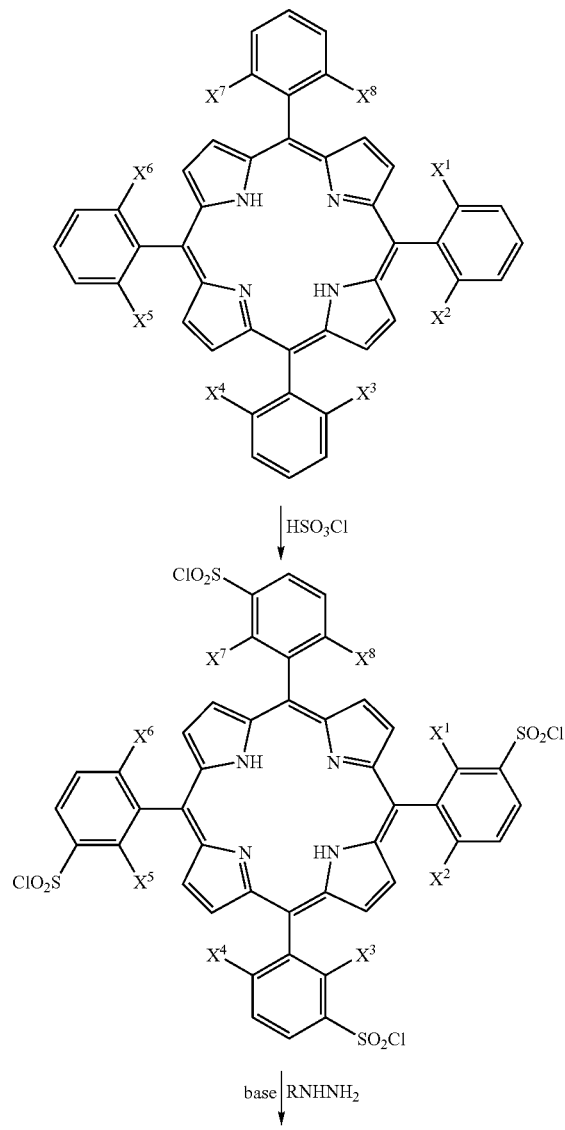

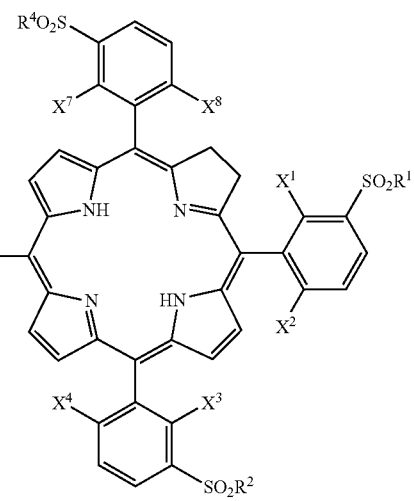

Also, by way of non limiting example, the chemical synthesis of the derivative complying with Formula (II) wherein:

$X^2$, $X^4$, $X^6$ and $X^8$ are chlorine atoms;

$X^1$, $X^3$, $X^5$ and $X^7$ are hydrogen atoms; and $R^1$, $R^2$, $R^3$, $R^4$ are —OH moieties, was conducted as follows:

5,10,15,20-tetrakis(2-chloro-3-chlorosulfonylphenyl)porphyrin (0.0658 g, 6.55×10$^{-5}$ mol) was dissolved in N,N-dimethylformamide, and/or pyridine and/or picoline (50 mL) dried and distilled beforehand. The temperature was raised from 50° C. to 150° C. Then, a solution of p-toluene sulfonyl hydrazide (130.0×10$^{-5}$ mol) and DABCO in DMF (5 mL) was added to the reaction mixture. The mixture was stirred at 150° C. under nitrogen atmosphere and sheltered from light. The evolution of the reaction was followed by spectroscopy of the visible region until the band Q at 750 nm reached its maximum.

Then, the solvent was evaporated and the reactive mixture was treated and the product obtained was hydrolysed with water to provide the requested product with a 77% output.

Mass spectroscopy (FAB), m/z: 1077 (central peak).

Vis-UV (buffer solution NaOH, $KH_2PO_4$), maximal wavelength (in nm): 353, 376, 486, 518, 604, 748.

Fluorescence quantum yield: 0.013

Lifetime of the triplet state in a nitrogen-saturated aqueous solution: 235 µs

Lifetime of the triplet state in an air-saturated aqueous solution: 3.88 µs

Quantum yield of the formation of singlet oxygen in a deuterated aqueous solution: greater than 30%.

Lifetime of singlet oxygen: 65 µs in deuterated water.

Also, schematically the reaction may be described as follows:

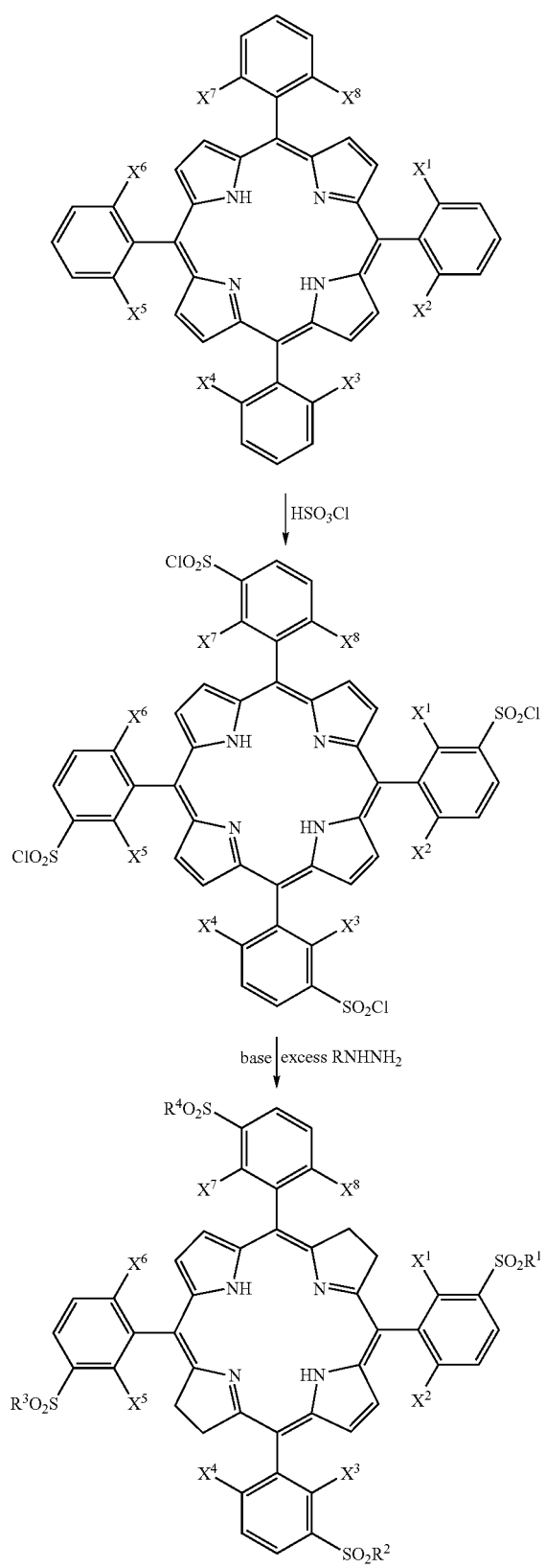

5,10,15,20-tetrakis(2-chloro-3-chlorosulfonylphenyl) porphyrin, used as starting porphyrin in the synthesis of chlorin and of bacteriochlorin described above, is known to the man of the art and has been described in the literature, in particular in the Journal of Heterocyclic Chemistry, 28: 635 (1991).

According to the present invention, the quanta yields of the formation of singlet oxygen were obtained by comparison between the phosphorescence intensity of singlet oxygen at 1270 nm wavelength in a solution containing the photosensitizer under study and the phosphorescence intensity obtained from another solution exhibiting the same absorptivity at the same wavelength, and including a reference photosensitizer.

According to the present invention, the reference photosensitizer used in meso-tetrakis(3-sulfophenyl)porphyrin (TPPS) whereof the value for the quantum yield of the formation of singlet oxygen in deuterated water is 0.64 at 7.4 pH (photochem. Photobiol, 70: 391, 1999).

The present invention also relates to an anticancerous and/or antiviral and/or antimicrobial medication for human or animal usage exhibiting as a main active agent one or several compounds described in the present invention.

This type of medication, used in particular in photodynamic therapy, may also contain one or several pharmaceutically acceptable excipients.

Naturally, other embodiments of the present invention, understandable to the man of the art, could have been contemplated without departing from the framework of the invention.

We claim:

1. A chlorin compound of Formula (I),

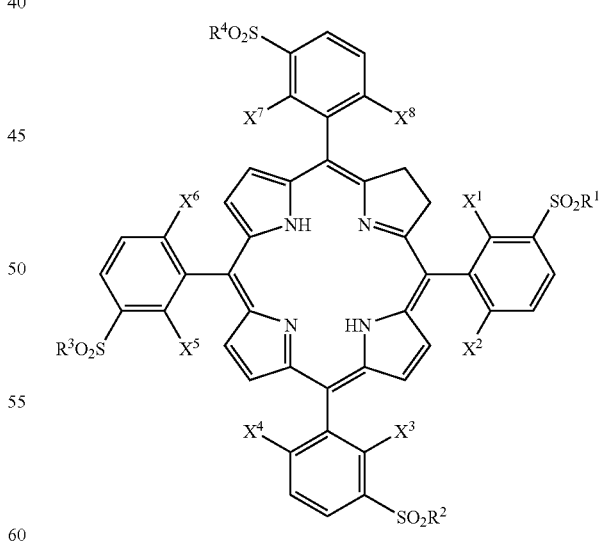

Formula (I)

wherein:

$X^1$, $X^2$, $X^3$, $X^9$, $X^5$, $X^6$, $X^7$, $X^8$ are each, identical or different, selected among halogen atoms, and/or hydrogen atoms, such that at least one of the radicals X of each pair $X^1/X^2$, $X^3/X^4$, $X^5/X^6$, $X^7/X^8$ is a halogen atom, $R^1$, $R^2$, $R^3$, $R^4$ are each, identical or different, selected among the moieties: —OH, amino acids, —OR and —NHR and/or chlorine atom, wherein R is an alkyl moiety having 1 to 12 carbon atoms.

2. The chlorin compound of claim 1, wherein:
$X^2$, $X^4$, $X^6$ and $X^8$ are chlorine atoms;
$X^1$, $X^3$, $X^5$ and $X^7$ are hydrogen atoms;
$R^1$, $R^2$, $R^3$, $R^4$ are chlorine atoms.

3. The chlorin compound of claim 1, wherein:
$X^2$, $X^4$, $X^6$ and $X^8$ are fluorine atoms;
$X^1$, $X^3$, $X^5$ and $X^7$ are hydrogen atoms;
$R^1$, $R^2$, $R^3$, $R^4$ are chlorine atoms.

4. The chlorin compound of claim 1, wherein:
$X^2$, $X^4$, $X^6$ and $X^8$ are fluorine atoms;
$X^1$, $X^3$, $X^5$ and $X^7$ are hydrogen atoms;
$R^1$, $R^2$, $R^3$, $R^4$ are —OH moieties.

5. The chlorin compound of claim 1, wherein:
$X^2$, $X^4$, $X^6$ and $X^8$ are chlorine atoms;
$X^1$, $X^3$, $X^5$ and $X^7$ are hydrogen atoms;
$R^1$, $R^2$, $R^3$, $R^4$ are —OH moieties.

6. The chlorin compound of claim 1, wherein:
$X^1$, $X^2$, $X^3$, $X^9$, $X^5$, $X^6$, $X^7$, $X^8$ are chlorine atoms'
$R^1$, $R^2$, $R^3$, $R^9$ are chlorine atoms.

7. The chlorin compound of claim 1, wherein
$X^1$, $X^2$, $X^3$, $X^4$, $X^5$, $X^6$, $X^7$, $X^8$ are chlorine atoms;
$R^1$, $R^2$, $R^3$, $R^4$ are —OH moieties.

8. A bacteriochlorin compound according to Formula (II),

Formula (II)

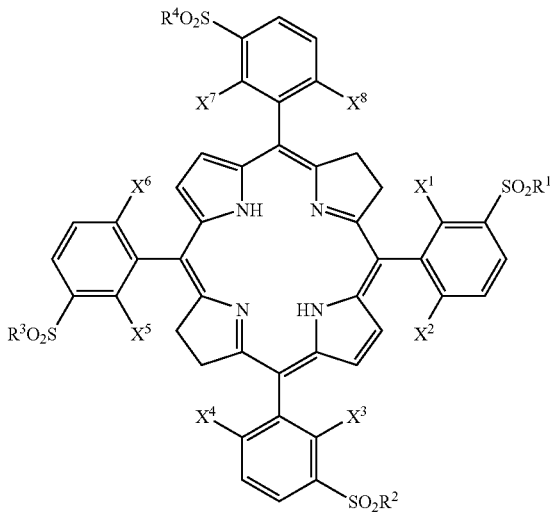

wherein:
$X^1$, $X^2$, $X^3$, $X^9$, $X^5$, $X^6$, $X^7$, $X^8$ are each, identical or different, selected among halogen atoms, and/or hydrogen atoms;

$R^1$, $R^2$, $R^3$, $R^4$ are each, identical or different, selected among the moieties: —OH, amino acids, —OR and —NHR and/or chlorine atom, wherein R is an alkyl moiety having 1 to 12 carbon atoms.

9. The bacteriochlorin compound of claim 8, wherein:
$X^1$, $X^2$, $X^3$, $X^4$, $X^5$, $X^6$, $X^7$, $X^8$ are each, identical or different, selected among halogen atoms and/or hydrogen atoms, such that at least one of the radicals X of each pair $X^1/X^2$, $X^3/X^4$, $X^5/X^6$, $X^7/X^8$ is a halogen atom.

10. The bacteriochlorin compound of claim 8, wherein:
$X^2$, $X^4$, $X^6$ and $X^8$ are chlorine atoms;
$X^1$, $X^3$, $X^5$ and $X^7$ are hydrogen atoms;
$R^1$, $R^2$, $R^3$, $R^4$ are chlorine atoms.

11. The bacteriochlorin compound of claim 8, wherein:
$X^2$, $X^4$, $X^6$ and $X^8$ are fluorine atoms;
$X^1$, $X^3$, $X^5$ and $X^7$ are hydrogen atoms;
$R^1$, $R^2$, $R^3$, $R^4$ are chlorine atoms.

12. The bacteriochlorin compound of claim 8, wherein:
$X^2$, $X^4$, $X^6$ and $X^8$ are chlorine atoms;
$X^1$, $X^3$, $X^5$ and $X^7$ are hydrogen atoms;
$R^1$, $R^2$, $R^3$, $R^4$ are —OH moieties.

13. The bacteriochlorin compound of claim 8, wherein:
$X^2$, $X^4$, $X^6$ and $X^8$ are fluorine atoms;
$X^1$, $X^3$, $X^5$ and $X^7$ are hydrogen atoms; —$R^1$, $R^2$, $R^3$, $R^4$ are —OH moieties.

14. The bacteriochlorin compound of claim 8, wherein:
$X^1$, $X^2$, $X^3$, $X^4$, $X^5$, $X^6$, $X^7$, $X^8$ are chlorine atoms'
$R^1$, $R^2$, $R^3$, $R^4$ are chlorine atoms.

15. The bacteriochlorin compound of claim 8, wherein:
$X^1$, $X^2$, $X^3$, $X^5$, $X^6$, $X^7$, $X^8$ are chlorine atoms;
$R^1$, $R^2$, $R^3$, $R^4$ are —OH moieties.

16. The bacteriochlorin compound of claim 8, the halogen atoms are selected from the group consisting of fluorine, chlorine and bromine.

17. A pharmaceutical composition comprising at least one chlorin compound according to claim 1 or a pharmaceutical acceptable salt thereof.

18. A pharmaceutical composition comprising at least one bacteriochlorin compound according to claim 8 or a pharmaceutical acceptable salt thereof.

19. A method of photodynamic therapy, comprising administering an effective amount of a compound of claim 1 to a human or animal and then irradiating said human or animal with light of a wavelength effective to activate said compound.

20. The method according to claim 19, wherein said human or animal has been diagnosed with cancer, and said compound is caused to accumulate preferentially in cancer cells of said human or animal.

21. The method according to claim 20, wherein said irradiating is effected by positioning a fiber optic element in proximity to said cancer cells.

22. A method of photodynamic therapy, comprising administering an effective amount of a compound of claim 8 to a human or animal and then irradiating said human or animal with light of a wavelength effective to activate said compound.

23. The method according to claim 22, wherein said human or animal has been diagnosed with cancer, and said compound is caused to accumulate preferentially in cancer cells of said human or animal.

24. The method according to claim 23, wherein said irradiating is effected by positioning a fiber optic element in proximity to said cancer cells.

25. A method of making chlorin compounds, comprising:
(a) chlorosulfonating a compound of the formula:

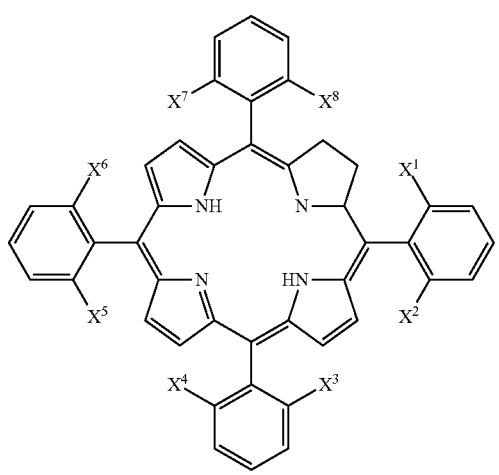

wherein $X^1$, $X^2$, $X^3$, $X^4$, $X^5$, $X^6$, $X^7$ and $X^8$ are each independently halogen or hydrogen;
(b) reducing the compound resulting from step (a) with hydrazide and at least one sterically hindered organic base; and
(c) coupling between the chlorosulfonated moiety of the compound resulting from step (b) and amines and/or amino acids and/or alcohols or hydrolyzing the chlorine of the chlorosulfonated moiety with water to produce a compound of the formula:

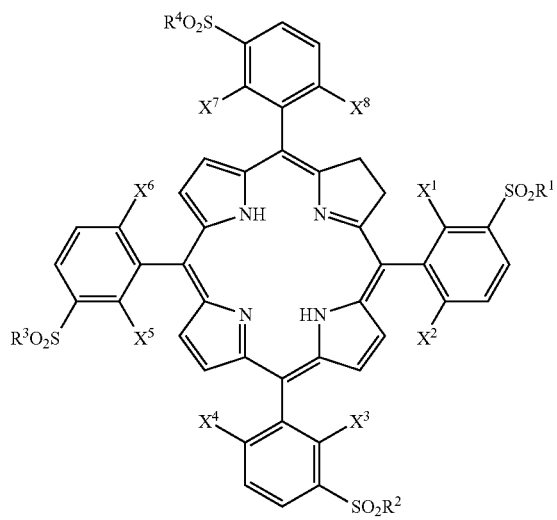

wherein $X^1$, $X^2$, $X^3$, $X^4$, $X^5$, $X^6$, $X^7$, and $X^8$
are as defined above and wherein $R^1$, $R^2$, $R^3$ and $R^4$ are each independently selected from the group consisting of —OH, amino acids, —OR, —NHR and chlorine, R being an alkyl moiety of 1 to 12 carbon atoms.

26. The method of claim 25, wherein the at least one sterically hindered organic base is selected from DABCO and DBU.

27. A method of making bacteriochlorin compounds, comprising:

(a) chlorosulfonating a compound of the formula:

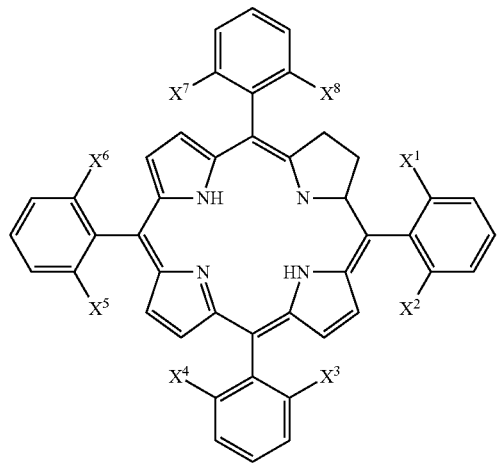

wherein $X^1$, $X^2$, $X^3$, $X^4$, $X^5$, $X^6$, $X^7$, and $X^8$ are each independently halogen or hydrogen;
(b) reducing the compound resulting from step (a) with hydrazide and at least one sterically hindered organic base; and
(c) coupling between the chlorosulfonated moiety of the compound resulting from step (b) and amines and/or amino acids and/or alcohols or hydrolyzing the chlorine of the chlorosulfonated moiety with water to produce a compound of the formula:

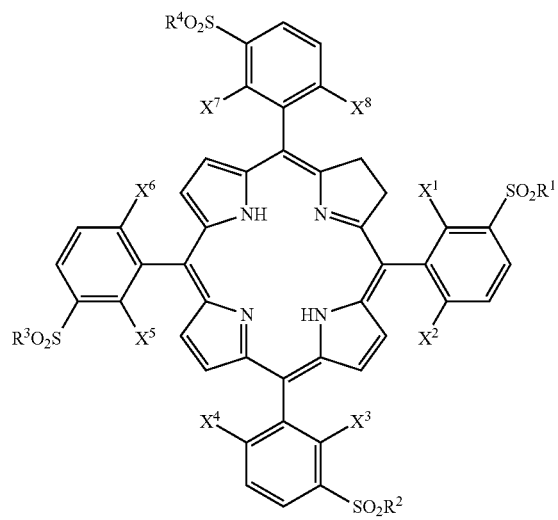

wherein $X^1$, $X^2$, $X^3$, $X^4$, $X^5$, $X^6$, $X^7$, and $X^8$
are as defined above and wherein $R^1$, $R^2$, $R^3$ and $R^4$ are each independently selected from the group consisting of —OH, amino acids, —OR, —NHR and chlorine, R being an alkyl moiety of 1 to 12 carbon atoms.

28. The method of claim 27, wherein the at least one sterically hindered organic base is selected from DABCO and DBU.

* * * * *

UNITED STATES PATENT AND TRADEMARK OFFICE
CERTIFICATE OF CORRECTION

PATENT NO. : 8,592,404 B2
APPLICATION NO. : 11/719295
DATED : November 26, 2013
INVENTOR(S) : Miguens Pereira et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1040 days.

Signed and Sealed this
Twenty-second Day of September, 2015

Michelle K. Lee
*Director of the United States Patent and Trademark Office*